US006936413B1

(12) United States Patent
Bischof et al.

(10) Patent No.: US 6,936,413 B1
(45) Date of Patent: Aug. 30, 2005

(54) METHODS AND SYSTEMS FOR PREPARING BLOOD PRODUCTS

(75) Inventors: Daniel F. Bischof, Bull Valley, IL (US); Ying-Cheng Lo, Green Oaks, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/004,696

(22) Filed: Dec. 5, 2001

(51) Int. Cl.[7] .......................... A01N 1/00; A61B 19/00
(52) U.S. Cl. ........................ 435/2; 604/410; 604/416
(58) Field of Search ........................... 435/2; 604/410, 604/416

(56) References Cited

U.S. PATENT DOCUMENTS

| 4,670,013 | A | | 6/1987 | Barnes et al. |
| 5,089,146 | A | | 2/1992 | Carmen et al. |
| 5,269,946 | A | | 12/1993 | Goldhaber et al. |
| 5,330,462 | A | | 7/1994 | Nakamura |
| 5,399,719 | A | | 3/1995 | Wollowitz et al. |
| 5,403,304 | A | | 4/1995 | Ishida |
| 5,405,343 | A | | 4/1995 | Mohr |
| 5,769,839 | A | * | 6/1998 | Carmen et al. ............. 604/408 |
| 5,908,742 | A | * | 6/1999 | Lin et al. ........................ 435/2 |
| 5,965,349 | A | | 10/1999 | Lin et al. |
| 6,251,580 | B1 | | 6/2001 | Lin et al. |
| 6,544,727 | B1 | | 4/2003 | Hei |
| 6,548,241 | B1 | * | 4/2003 | McBurney et al. ............. 435/2 |
| 2002/0138066 | A1 | * | 9/2002 | Manica et al. .............. 604/410 |

FOREIGN PATENT DOCUMENTS

| WO | 90/00059 | * | 1/1990 |
| WO | WO 91/15182 A1 | | 10/1991 |
| WO | WO 92/19355 A1 | | 11/1992 |
| WO | WO 96/39940 A1 | | 12/1996 |
| WO | PCT/US02/37554 | | 3/2003 |

OTHER PUBLICATIONS

Lin et al., "Photochemical Inactivation of Viruses and Bacteria in Platelet Concentrates by Use of a Novel Psoralen and Long-Wavelength Ultraviolet Light," TRANSFUSION, vol. 37, pp. 423-435, Apr. 1997.
U.S. Appl. No. 10/008,361, filed Dec. 05, 2001, Bischof et al.
U.S. Appl. No. 10/741,683, filed Dec. 19, 2003, Blickhan et al.

* cited by examiner

Primary Examiner—Sandra Saucier
(74) Attorney, Agent, or Firm—Andrew G. Kolomayets; Michael C. Mayo; Bradford R. L. Price

(57) ABSTRACT

Methods and systems for preparing blood products that are ready for treatment in established pathogen inactivation procedures are disclosed. The methods include providing a source of a blood component and combining the blood component with a synthetic medium in a selected ratio of the blood component to the synthetic media, whereby the resulting blood product is treatment-ready.

8 Claims, 10 Drawing Sheets

METHODS AND SYSTEMS FOR PREPARING BLOOD PRODUCTS

The present invention generally relates to methods and systems for preparing blood products that are ready for treatment in established pathogen inactivation procedures, are suitable for extended storage and readily transfusable to a patient.

BACKGROUND OF THE INVENTION

Human whole blood is made up of several different components, including red blood cells, white blood cells and platelets. These blood components are suspended in plasma, the liquid medium component of blood. As used herein, the term "component" includes plasma.

Whole blood collected from healthy donors is routinely separated into its components, and one or more of the separated components are used for later administration (transfusion) to a patient who may be in need of the particular component. For example, red blood cells may be administered to a patient to replace blood loss or to treat patients with chronic anemia. Plasma may be administered to treat clotting factor deficiencies. Platelets are commonly administered as a therapy to cancer patients whose ability to generate platelets has been compromised by chemotherapy.

Blood components can be separated and collected by so called "manual" methods or by "apheresis." For example, in a manual system for collecting platelets, whole blood is withdrawn from a donor and then separated (by, for example, centrifugation) into platelets (suspended in plasma) and red blood cells. The separated platelets are collected and typically stored until administration to the patient. The collected platelets from several "random" donors are often pooled to provide a single therapeutic dose for a patient. A "therapeutic dose" of platelets (i.e., the number of platelets transfused to a patient in a single transfusion) is generally understood to mean anywhere between $2.0$–$4.0 \times 10^{11}$ and, more typically, approximately $3 \times 10^{11}$ platelets. The term "therapeutic dose," as used herein, however, is not limited to the above-identified number of platelets, but includes any number of platelets that may be administered to a patient as part of a therapy.

Platelets (as well as other blood components) can also be collected by "apheresis." In apheresis, whole blood is withdrawn from a donor and passed through a disposable fluid circuit that includes a phlebotomy needle for insertion into the donor, tubing and interconnected containers. The fluid circuit is associated with a separation device. The withdrawn whole blood is introduced into the separation device where it is separated into its desired components. In platelet apheresis, the separated platelets are collected in the separation device and/or pre-attached collection containers.

During a platelet apheresis procedure, the donor remains "connected" to the device, and red cells and some plasma are returned to the donor. Return of the other components such as red cells and plasma provides for a continuous process and allows a greater volume of blood to be processed. As a result, in a platelet apheresis procedure, unlike a manual collection, a therapeutic dose of about $3 \times 10^{11}$ platelets can be collected from a single donor. Such platelets are sometimes referred to as "single donor platelets." In fact, some of today's apheresis systems also allow for collection of a "double dose" or even a "triple dose" of single donor platelets.

Red blood cells have traditionally been collected by manual methods. More recently, however, systems and methods have been developed to allow for the collection of red blood cells by apheresis. Whether collected manually or by apheresis, the red cells are separated from platelets and plasma, collected and usually stored until later administration to a patient.

There are several commercially available apheresis systems. One of the earliest and still widely used systems is the CS3000® Blood Cell Separator available from Baxter Healthcare Corporation of Deerfield, Ill. Baxter Healthcare Corporation also makes and sells the Amicus® Separator. Both the CS3000® and Amicus® are used in the collection of platelets and plasma. The Alyx™ device, also made by Baxter Healthcare Corporation, is a portable apheresis device adapted for the collection of red blood cells as well as other blood components. The Alyx™ device is generally described in U.S. Pat. No. 6,294,094, which is incorporated herein by reference.

Other apheresis systems, such as the COBE Spectra and COBE Trima are available from COBE Laboratories, Inc. (a division of Gambro) of Arvada, Colo. Fresenius AG, of Bad Homburg, Germany, sells apheresis systems under the product designations AS-104 and the AS.TEC-204. Haemonetics Corporation of Braintree, Mass., sells a device under the name MCS Plus. All of the above apheresis systems are believed to be capable of providing at least one therapeutic dose of about $3 \times 10^{11}$ platelets suspended in plasma. At least some of the above-described apheresis systems may also be adapted to collect red blood cells.

Whether collected manually or by apheresis, before transfusion to a patient, the collected blood component may be subjected to an additional treatment to ensure the safety of the blood component (e.g., platelets, plasma, red blood cells) intended for transfusion. Specifically, the collected blood components are treated to remove or otherwise inactivate virus and/or bacteria ("pathogens") which may reside in the particular blood component. Many of the pathogen inactivation methods involve combining the platelets with a chemical compound which acts directly on the pathogen, or adding a photoactivation compound which, when stimulated by light, acts on the pathogen.

These pathogen inactivation methods have been developed to provide a blood product that is substantially free of pathogens. These methods are subject to government regulatory review and approval. By way of example, a method for the inactivation of pathogens in red blood cells is described in U.S. Pat. No. 6,093,725, which is incorporated herein by reference. A method for the inactivation of pathogens in platelets and plasma is described in U.S. patent application Ser. No. 09/325,325, filed Jun. 3, 1999, also incorporated by reference herein. That method utilizes a photoactivated psoralen compound that is added to blood platelets and/or blood plasma. The platelets with psoralen compound are contacted with light of a specific wavelength (e.g., UV-A) to activate the psoralen compound and, consequently, inactivate pathogens present in the blood product. In this method for pathogen inactivation using psoralen photoactivation compounds, the collected platelets (in plasma) are combined with a specific quantity of a synthetic storage medium. The relative quantities and/or ratio of synthetic storage medium and plasma in which the platelets are suspended are selected to enhance the efficacy of the pathogen inactivation method, as well as to maintain the viability of the platelets during storage, and prior to transfusion.

In the above-described platelet pathogen inactivation method, the ratio of synthetic storage medium and plasma provides an environment that enhances the activation of the photochemical compound and results in increased viral and bacterial kill. The synthetic storage medium (with plasma) also provides and/or helps maintain favorable physiologic conditions, such as pH, buffering and sources of nutrients which are conducive to effecting pathogen inactivation and/or to sustaining platelet metabolism and viability during extended storage.

Unfortunately, not all apheresis procedures and systems currently used result in a (pathogen inactivation) treatment-ready blood product. For example, in the context of platelet collection, not all apheresis procedures result in a platelet product that includes a therapeutic or otherwise acceptable dose of platelets that is suspended in a suitable synthetic medium and in the desired relative quantities and/or ratio of synthetic medium and plasma. Thus, in order to treat the collected platelets in an established platelet pathogen inactivation procedure, one may first have to "convert" such platelets to obtain a "treatment-ready" platelet product. Likewise, in the context of other blood products (e.g., red blood cells) it may also be necessary to "convert" the collected blood component to one that is suitable for treatment in established methods of pathogen inactivation of the given blood component.

Thus, it would be desirable to provide a method and system to allow for easy preparation of such treatment-ready blood products, regardless of the method used to collect the source blood component. The resulting "converted" product is one that is (1) suitable for treatment using established pathogen inactivation protocols, (2) suitable for extended storage, if necessary, and, (3) suitable for transfusion to a patient.

SUMMARY OF THE INVENTION

In one aspect, the present invention is directed to a method for preparing a pathogen inactivation treatment-ready blood product. The method includes providing a container system that has at least an interim container and a container including a synthetic medium. The synthetic medium container is in flow communication with the interim container. The method further includes providing a source container including a quantity of blood or blood component that is separate from the container system. The source container and interim container are placed in flow communication and the blood or blood component is transferred to the interim container. The method includes combining the quantity of the blood or blood component with a selected quantity of the synthetic medium to provide the selected ratio of medium and blood component (and, thus, the treatment-ready blood product).

In another, more specific aspect, the present invention is directed to a method for preparing a blood product that includes platelets, a synthetic storage medium and plasma. The method includes providing a container system that has an interim container and a container including a liquid synthetic storage medium. The synthetic storage medium container is in flow communication with the interim container.

The method further includes providing a source container including platelets suspended in plasma. In accordance with the method, the source container is attached to the interim container and the platelets in plasma are transferred to the interim container. The platelets in plasma are combined with the synthetic storage medium in a selected ratio.

In another aspect, the present invention is directed to a container system for preparing a platelet product that includes platelets, a synthetic storage medium and plasma. The system includes an empty interim container in flow communication with a container that includes a synthetic storage medium. The container system further includes a flow path between the empty interim container and the synthetic storage medium container. The interim container is adapted for connection to a platelet source that includes at least one therapeutic dose of platelets.

DETAILED DESCRIPTION OF THE DRAWINGS

It will be appreciated that the present invention finds application in the processing of any blood components including red blood cells, plasma and platelets. Red cells, plasma or platelets collected manually or by apheresis can be converted to a pathogen inactivation treatment-ready blood product. In one preferred, but non-limiting embodiment, the present invention is directed to methods and systems for preparing a treatment-ready platelet product. Accordingly, the description that follows is, in large part, set forth in the context of preparing a treatment-ready platelet product. Of course, it will be understood that other embodiments directed to the preparation of other blood products are also possible and within the scope of the present invention.

Figure 1:
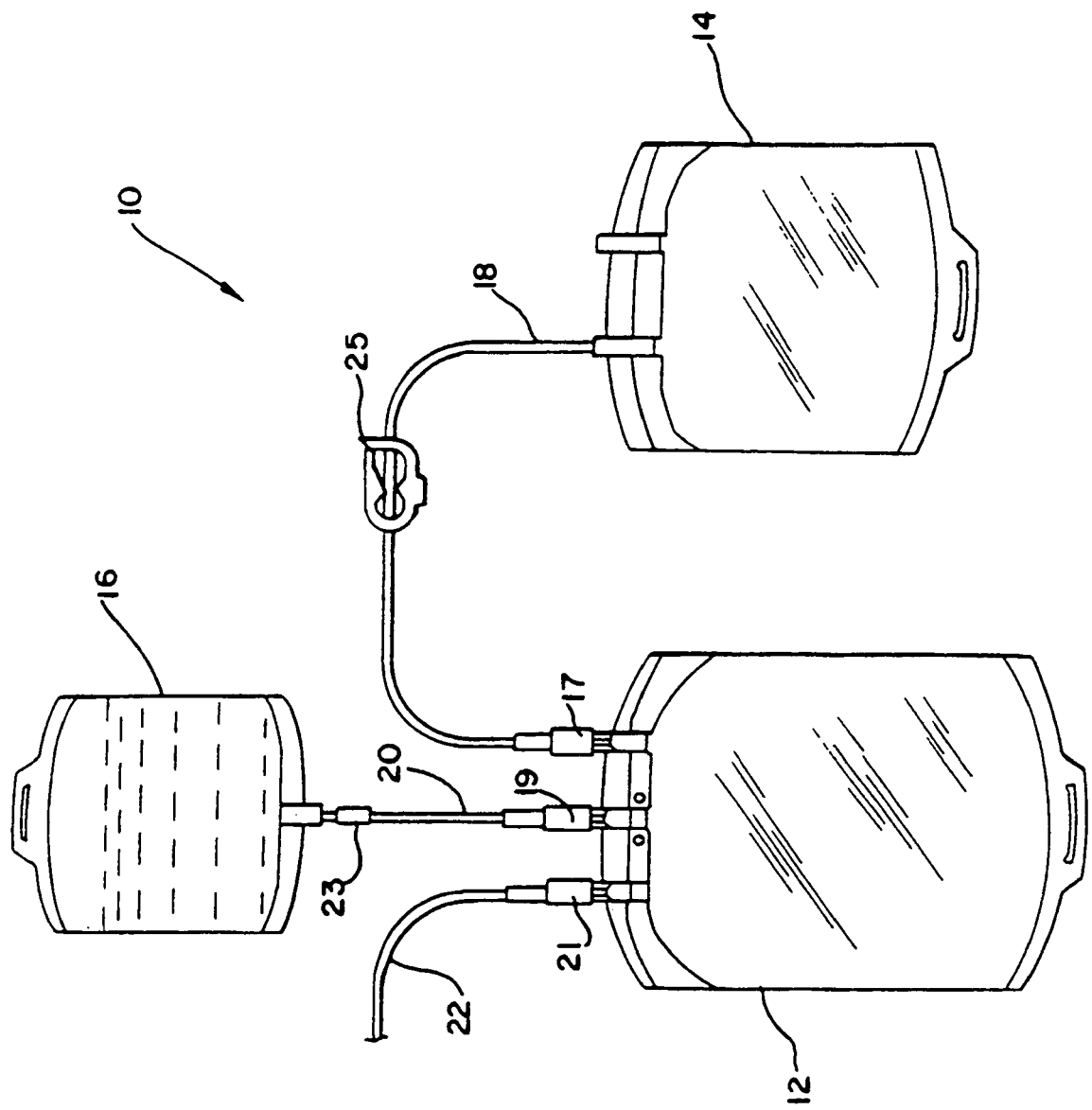
FIG. 1 is a plan view of a container system embodying the present invention.

Turning now to the figures, shown in FIG. 1 is just one example of a container system 10 embodying the present invention. As shown in FIG. 1, in one embodiment, container system 10 includes an empty interim container 12, a synthetic storage medium container 16 and an empty excess fluid container 14. The containers 12, 14 and 16 are interconnected by tubings 18 and 20, which provide flow paths between the interim container and the two satellite containers, 14 and 16.

Tubings 18 and 20 may be associated with devices for controlling liquid flow therethrough. As shown in FIG. 1, tubings may include flow control devices 23 and 25. Flow control device may be a frangible connector 23 which, when broken, establish an open flow path through the tubing. Frangible connectors are described in U.S. Pat. No. 4,294,247. Flow control device may also be a clamp 25, such as Roberts-type clamps, as described, for example, in U.S. Pat. No. 3,942,228. FIG. 1 shows one embodiment of the placement of flow control devices. It will, of course, be understood that the type of device used and its location may be determined by one of ordinary skill, as necessary or desired.

The containers of container system 10 may be made of biocompatible materials suitable for use in the medical field, including, but not limited to, polyvinyl chloride (PVC) based materials and non-PVC based materials. The container material should be one that can be sterilized by known sterilization techniques such as (but not limited to) autoclaving. Alternatively, filled container 16 may be autoclaved and the empty containers may be sterilized by other forms of sterilization such as electron beam or gamma radiation. Container system 10 may be assembled by joining the separately sterilized portions and sterilizing the point of connection by, for example, electron beam in the manner described in U.S. Pat. No. 5,009,654, which is incorporated by reference herein.

The internal volumes of the containers may vary as necessary and will depend on the volume of blood product or other solution to be stored or introduced into the given container. Interim container 12 may be empty and may have an internal volume sufficient to hold the volume of blood product collected by apheresis or by other (e.g., manual) blood collection procedures. In one preferred embodiment, where the blood component collected includes platelets in plasma, interim container 12 may have an internal volume sufficient to hold between about 500 ml and 1 liter of liquid.

In one preferred embodiment, interim container 12 may be made of a thermoplastic material such as polyvinyl chloride (PVC) that has been plasticized with a plasticizer such as DEHP, TEHTM, or a citrate ester including, but not limited to, n-butyryltri-n-hexyl citrate. Containers made from such plasticized PVC are available from Baxter Healthcare Corporation of Deerfield, Ill., under the product codes PL-146, PL-1240 and PL-2209. Of course, other thermoplastic materials may also be used to make interim container 12, including a styrene ethylene butylene styrene (SEBS) block copolymer such as KRATON® or other polyolefin copolymer blended with ethylene-vinyl-acetate and polypropylene. Still another example of a suitable material for use in container 12 is one that includes the SEBS block copolymer described above blended with ultra-low density polyethylene and ethylene vinyl acetate. Such containers are also available from Baxter Healthcare Corporation of Deerfield, Ill., under the codes PL-732 and PL-2410, respectively.

Figure 2:
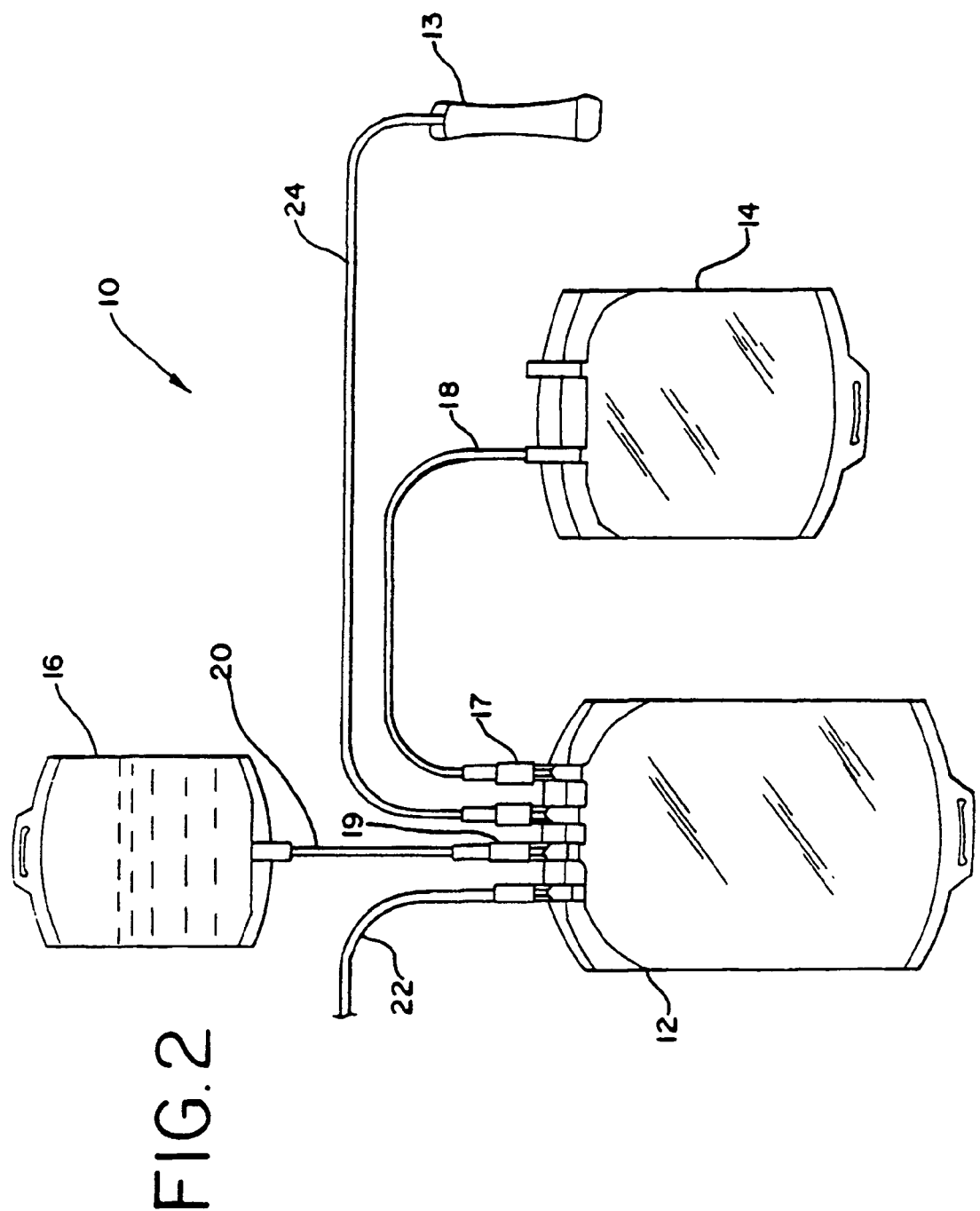
FIG. 2 is a plan view of an alternative container system embodying the present invention.
Figure 10:
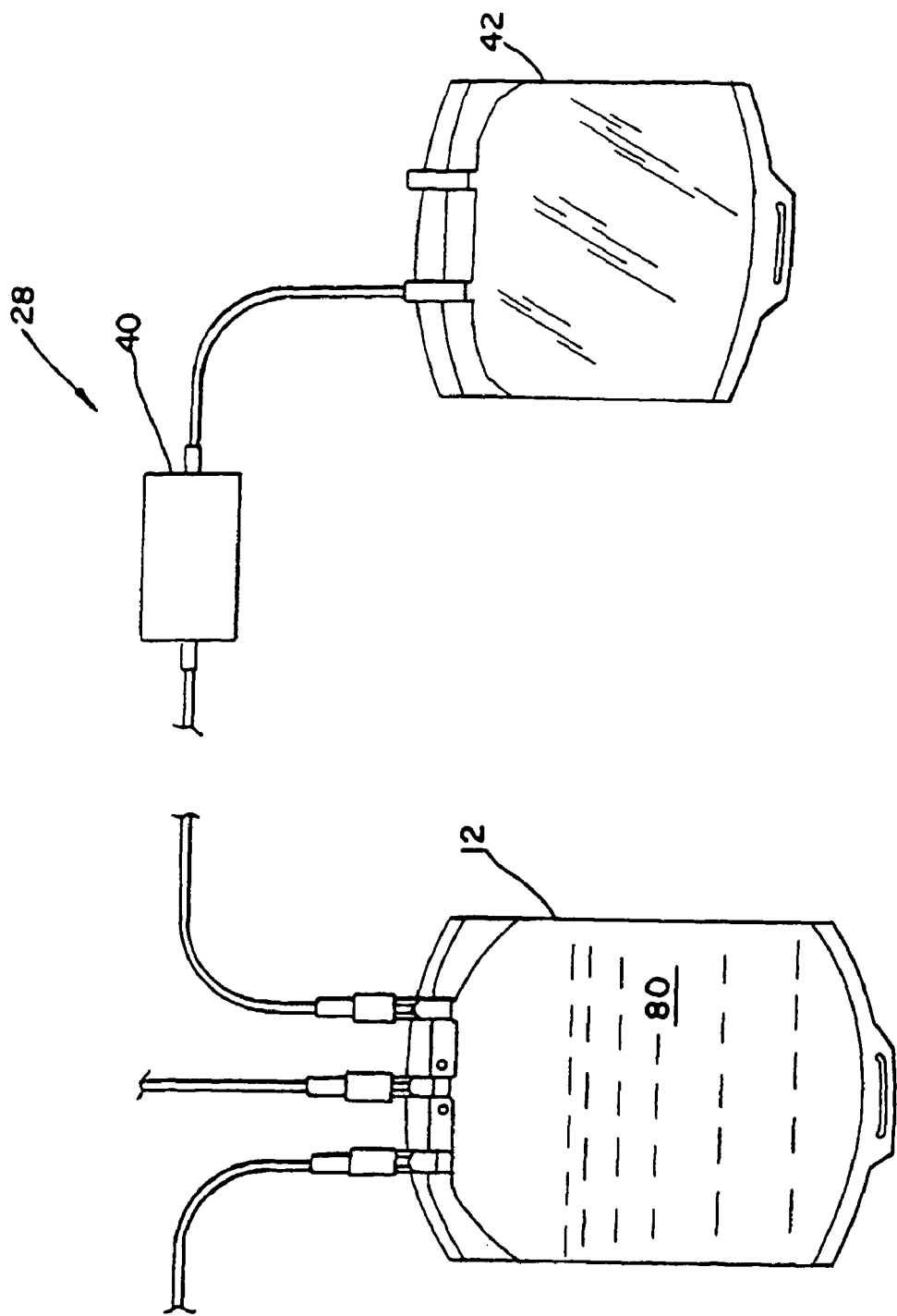
FIG. 10 is a plan view of a container system embodying the present invention prior to attachment to a processing set for a pathogen inactivation treatment.

As shown in FIG. 1, container 12 may include several tubing ports 17 and 19 with plastic tubings 18 and 20 extending therefrom and communicating with the other containers 14 and 16. Container 12 may further include a tubing port 21 and associated tube 22 for attachment to a blood component source 26, as shown, for example, in FIG. 5. Container 12 may also include a separate port and tube (not shown) for attachment to a disposable processing set for pathogen inactivation treatment 28 (FIG. 10). Alternatively, one of the existing tubings 18, 20 or 22 may be used for such attachment. Optionally, as shown in FIG. 2, container system 10 may also include a sampling pouch 13 for sampling the blood component in interim container 12. Sampling pouch 13 may be pre-attached to interim container 12 by tubing 24.

In a preferred embodiment, shown in FIG. 1, container system 10 includes an empty excess fluid container 14. In one embodiment, where the blood component collected includes platelets suspended in plasma, the excess fluid container 14 should have an internal volume sufficient to hold whatever quantity of excess plasma transferred from interim container 12, as will be described in more detail below. For example, in one such embodiment, excess fluid container 14 may have an internal volume sufficient to hold approximately 400 ml of fluid.

Excess fluid container 14 may be made of any thermoplastic material. One preferred material is a thermoplastic material that includes plasticized polyvinyl chloride. Containers of this type are also available from Baxter Healthcare Corporation of Deerfield, Ill., under the code PL-146 or PL-1240. Of course other suitable plastic materials may also be used.

Synthetic medium container 16 is provided as a filled container of a liquid synthetic medium for use in the processing of the collected blood component. Preferably, synthetic medium container 16 may have an internal volume sufficient to hold the quantity of medium needed for combination with the blood component. For example, where the blood product collected is platelets in plasma, container 16 may hold at least approximately 250 ml of a synthetic storage medium. Synthetic medium container 16 may be made of any suitable, biocompatible thermoplastic material. Preferably, one such material includes the plasticized PVC material described above. Other suitable materials include a blend of ultra-low density polyethylene, polypropylene, polyamide and the SEBS copolymer previously described. Containers made of such materials are available from Baxter Healthcare Corporation of Deerfield, Ill., under the product codes PL-146, PL-1240 and PL-2411.

The synthetic medium itself may be any medium suitable and useful in the processing, treatment, conditioning and/or storage of the blood component. For example, the liquid synthetic medium may be one that enhances the subsequent pathogen inactivation treatment of the component. Alternatively, the liquid synthetic medium may be a storage medium designed to extend the life of the blood component during storage. The liquid synthetic medium may also be one that both enhances the efficacy of the pathogen inactivation treatment and extends the storage life of the blood product.

In the case of preparing a treatment-ready platelet product, the synthetic storage medium may be any medium that is suitable for extended storage of platelets. Examples of suitable storage media are described in U.S. Pat. Nos. Re. 32,874, 4,695,460, 4,828,976, all of which are incorporated herein by reference. Other suitable media include a sodium chloride, sodium acetate and sodium citrate solution.

Where the source blood component is red blood cells, still other synthetic media may be used to condition the red blood cells for pathogen inactivation. Examples of suitable solution are those described in U.S. Pat. Nos. 5,906,915 and 4,267,269, which are also incorporated herein by reference. Particularly preferable in the preparation and conditioning of a treatment-ready red blood cell product is a solution like the one described in U.S. Pat. No. 5,906,915 which includes at least sodium citrate, sodium phosphate monobasic, sodium phosphate dibasic, adenine and mannitol and, optionally, dextrose. Most preferred is a solution that includes approximately 25 mM sodium citrate dihydrate, approximately 4.4 mM sodium phosphate monobasic, approximately 16 mM sodium phosphate dibasic, approximately 1.5 mM adenine, approximately 39.9 mM mannitol and optionally, approximately 45.4 mM dextrose, having a pH of 7.0–7.5, and preferably approximately 7.3–7.5. This solution is known as Erythrosol (or E-Sol) and is available from Baxter Healthcare Corporation. E-Sol may be added to red blood cells as two separate parts. Part I, sometimes referred to as E-Sol A, includes approximately 26.6 mM sodium citrate, approximately 17.0 mM sodium phosphate dibasic, approximately 4.7 mM sodium phosphate, approximately 1.6 mM adenine and approximately 42.5 mM mannitol, and Part II includes the dextrose. The pH of E-Sol A may be approximately 7.0–7.5, and, preferably, approximately 7.3–7.5. The above compositions can also be made by modifying the above concentrations by ±15%.

A preferred storage medium for the storage of platelets is one that includes sodium chloride, sodium citrate, sodium acetate and sodium phosphate. More preferably, the synthetic storage medium is one that includes between approximately 45–120 mM sodium chloride, 5–15 mM sodium citrate, 20–40 mM sodium acetate and 20–40 mM sodium phosphate, having a pH of approximately 7.0–7.4, and preferably approximately 7.2.

In an even more preferred embodiment, the synthetic platelet storage medium may include approximately 70–90 mM sodium chloride, approximately 8–12 mM sodium citrate, approximately 25–35 mM sodium acetate and approximately 22–35 mM sodium phosphate (which can be a combination of various protonated sodium phosphate species, such as dibasic sodium phosphate and monobasic sodium phosphate. The pH of such solution is a approximately 7.0–7.4 and preferably, approximately 7.2. Most preferred is a synthetic storage medium that has any pH of approximately 7.2 and the formulation set forth in Table 1 below.

TABLE I

| Component | Molarity (approx.) (mM) |
| --- | --- |
| Dibasic Sodium Phosphate, Anhydrous | 21.5 |
| Monobasic Sodium Phosphate, Monohydrate | 6.7 |
| Sodium Citrate, Dihydrate | 10.8 |
| Sodium Acetate, Trihydrate | 32.5 |
| Sodium Chloride | 77.3 |

Storage media of the type described above are available from Baxter Healthcare Corporation of Deerfield, Ill., under the name Intersol™. Of course, it will be understood that the formulations described above are the initial formulations for the media and that due to pH changes and adjustments, the ratio of acid to conjugate base of some of the ingredients may shift, thus altering the initial formulation during preparation and storage.

The platelet storage medium described above is effective to extend the life of the collected platelets during storage to at least 5 days and possibly up to approximately 7 or more days. It is also effective in enhancing the efficacy of pathogen inactivation in certain established platelet pathogen inactivation procedures and protocols, particularly for those protocols that utilize a psoralen such as, 5'-(4-amino-2-oxa) butyl-4,5',8-trimethyl psoralen as the pathogen inactivation compound. Examples of such pathogen inactivation protocols are described in U.S. Pat. Nos. 5,578,736 and 5,593,823, both of which are incorporated herein by reference.

For example, it has been discovered that given a fixed concentration of photochemical compound (e.g., psoralen) and a substantially constant and reproducible dose of ultraviolet (UVA) light, pathogen inactivation is improved when some of the plasma in which the collected platelets are suspended is removed and substituted with a synthetic storage medium of the type described herein. At the same time, it has been discovered that some plasma is required to maintain in vitro platelet function. Thus, a balance between inactivation efficiency and maintenance of in vitro platelet function has been obtained and has become part of these established platelet pathogen inactivation protocols.

To achieve this balance, certain established pathogen inactivation protocols for platelets require that the platelets be suspended in a selected quantity of the synthetic medium relative to the quantity of plasma. In one such established method, the final platelet product includes platelets suspended approximately 50–80% (by volume) of a synthetic platelet storage medium that includes sodium chloride, sodium citrate, sodium acetate and sodium phosphate and approximately 20–50% (by volume) of plasma. More preferably, the final platelet product includes platelets suspended in approximately 60–70% (by volume) of a synthetic platelet storage medium that includes sodium chloride, sodium citrate, sodium acetate and sodium phosphate and approximately 30–40% (by volume) of plasma. In an even more preferred embodiment, where the pathogen inactivation protocol utilizes 5'-(4-amino-2-oxa) butyl-4,5',8-trimethyl psoralen as the pathogen inactivation compound, the treatment-ready platelet product should include platelets suspended in approximately 65% (by volume) of a synthetic medium of the type set forth in Table 1 above approximately and 35% (by volume) of plasma.

The synthetic media 22, optionally mixed with plasma, can condition the platelet concentrate for other pathogen inactivating systems employing other types of pathogen inactivating compounds. For example, other pathogen inactivating systems can employ other pathogen inactivating compounds such as phthalocyanine derivatives, phenothiazine derivatives (including methylene blue or dimethyl-methylene blue); endogenous and exogenous photosensitizers such as alloxazines, isoalloxazines (including riboflavin), vitamin Ks, vitamin L, napththoguinones, naphthalenes, naphthols, and other pathogen inactivating compounds disclosed in U.S. Pat. Nos. 6,258,577, 6,268,120, and 6,277,337, which are incorporated herein by reference, or "Pen 110," which is made by V.I. Technologies, Inc. (which is also known as the Inactine™ compound).

Examples of pathogen inactivation compounds that may be useful in red blood cell pathogen inactivation methods include the pathogen inactivation agents disclosed above and those disclosed in U.S. Pat. No. 6,093,725 and U.S. application Ser. No. 09/539,226 filed Mar. 30, 2000, which is directed to the use of compounds having nucleic acid affinity and containing a mustard group, or mustard group equivalent or mustard group intermediate. U.S. Pat. No. 6,093,775 and U.S. application Ser. No. 09/539,226 are incorporated herein by reference. A preferred compound for red blood cell pathogen inactivation is p-alanine, N-(acridin-9-yl), 2-[bis(2-chloroethyl)amino] ethyl ester.

Figure 5:
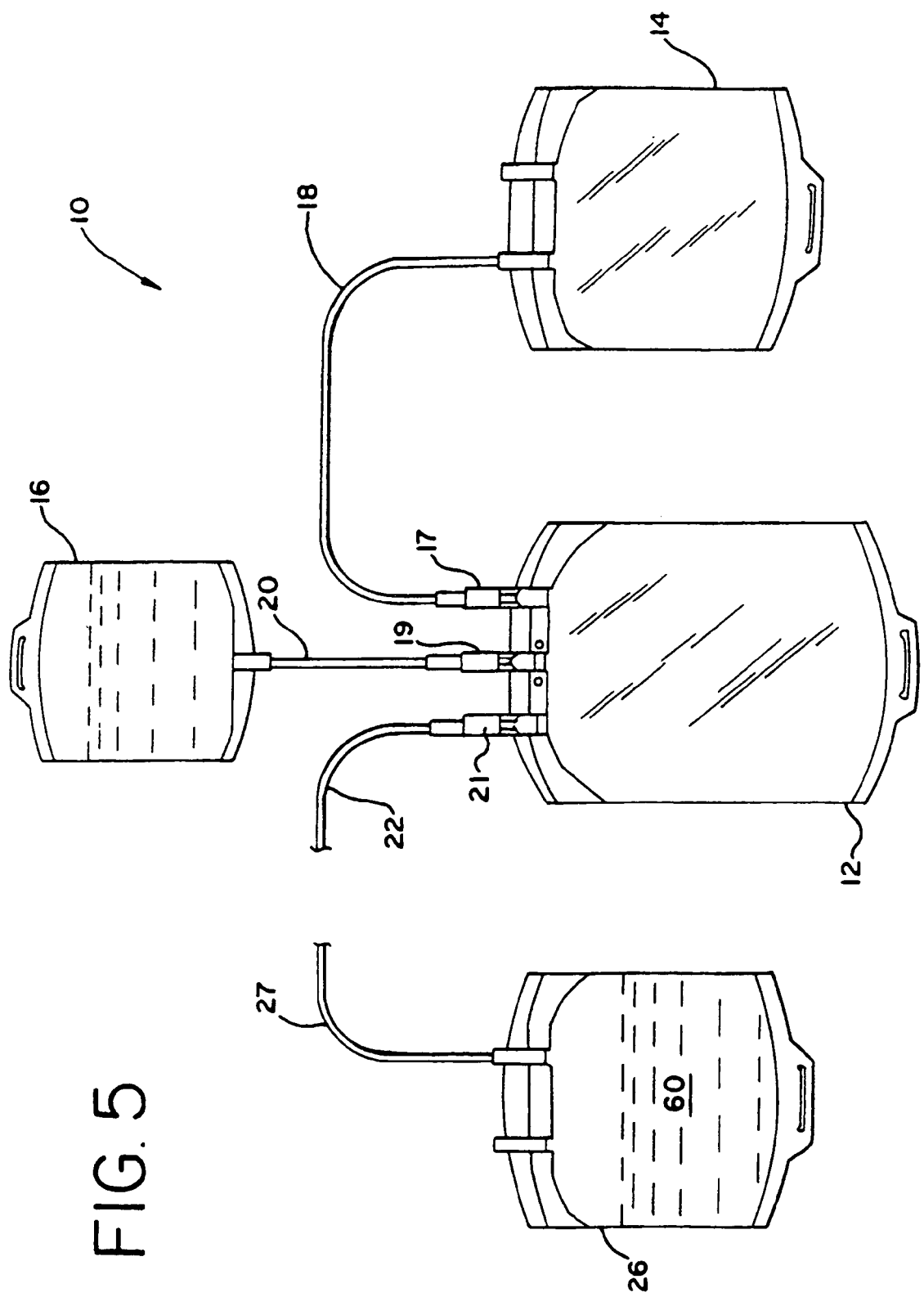
FIG. 5 is a plan view of the container system of FIG. 1 prior to attachment of a platelet source.

Turning now to the method of preparing a treatment-ready blood product such as platelets in accordance with the present invention, interim container 12 of container system 10 is adapted for attachment to a source of collected platelets 26 (FIG. 5). Source container 26 may be attached to the interim container 12 by joining tubings 22 and 27 in a sterile manner. Methods and systems for joining tubing in, preferably, a sterile manner are well known in the field of blood processing. One particularly useful system for attaching the tubings of interim container 12 and source container 26 is the Terumo SCD 312 sterile connection device generally described in U.S. Pat. No. 5,802,689, which is incorporated by reference herein. Other possible means for sterile connection will also be known and recognized by those of ordinary skill in the art. In any event, once the sterile connection is made, source platelets from source container 26 are transferred to interim container 12.

Container system 10 and the associated method of preparing a blood product finds particular application for preparing platelet products from source platelets that include at least a standard therapeutic dose of approximately $3 \times 10^{11}$ platelets suspended in a volume of plasma. As indicated above, a therapeutic dose of approximately $3 \times 10^{11}$ platelets may be made up from several units of pooled random donor platelets. More preferably, such platelets are obtained by apheresis using apheresis machines such as the Baxter CS3000, the Baxter Amicus®, the COBE Spectra, the COBE Trima, the Haemonetics MCS Plus and the Fresenius AS-104, AS-204 and Com.tec. Some apheresis systems of the type identified above are described, for example, in U.S. Pat. Nos. 5,704,889, 5,496,265, 5,720,716 and 6,113,554.

However, platelets collected using some of these commercially available apheresis systems are often suspended in more than a desirable quantity of plasma and, such systems do not have readily available means for adding the selected amount or even an acceptable type of synthetic medium. For example, depending on the apheresis device used, the platelets may be more or less concentrated and, consequently, may include less or more plasma. Most typically, however, the volume of collected plasma (which includes the platelets) is approximately 300 ml. Platelets stored in approximately 300 ml of plasma may not be acceptable for treatment as part of certain established methods for pathogen inactivation, particularly those that use a psoralen photoactivation compound. For purposes of pathogen inactivation using such established methods as well as for storage, the platelet product must be suspended in the selected quantities (and/or ratio) of synthetic medium and plasma. In short, the platelet product obtained must, in many instances, be "converted" to a platelet product suitable for treatment (i.e., "treatment-ready") in such established protocols and suitable for extended storage.

Thus, in one embodiment of the present invention, source platelets that include an excess amount of plasma must have some of the excess plasma removed prior to addition of the synthetic storage medium. Thus, after connection (e.g., sterile) of source container 26 to interim container 12 and the transfer of approximately 250–350 ml of platelets suspended in plasma (designated as 60 in FIG. 5), the platelets in plasma residing in interim container 12 may be centrifuged to separate excess plasma from the platelets. During centrifugation, flow control devices 23 and 25 (FIG. 1) are in the closed position to prevent flow of fluid from interim container 12. In one embodiment, a Sorval RC 3B Plus centrifuge may be spun at approximately 3800 rpm for approximately 6 minutes to achieve sufficient separation of platelets from plasma. Of course, other speeds, "9" forces and centrifugation times may also be employed to achieve such separation.

Figure 6:
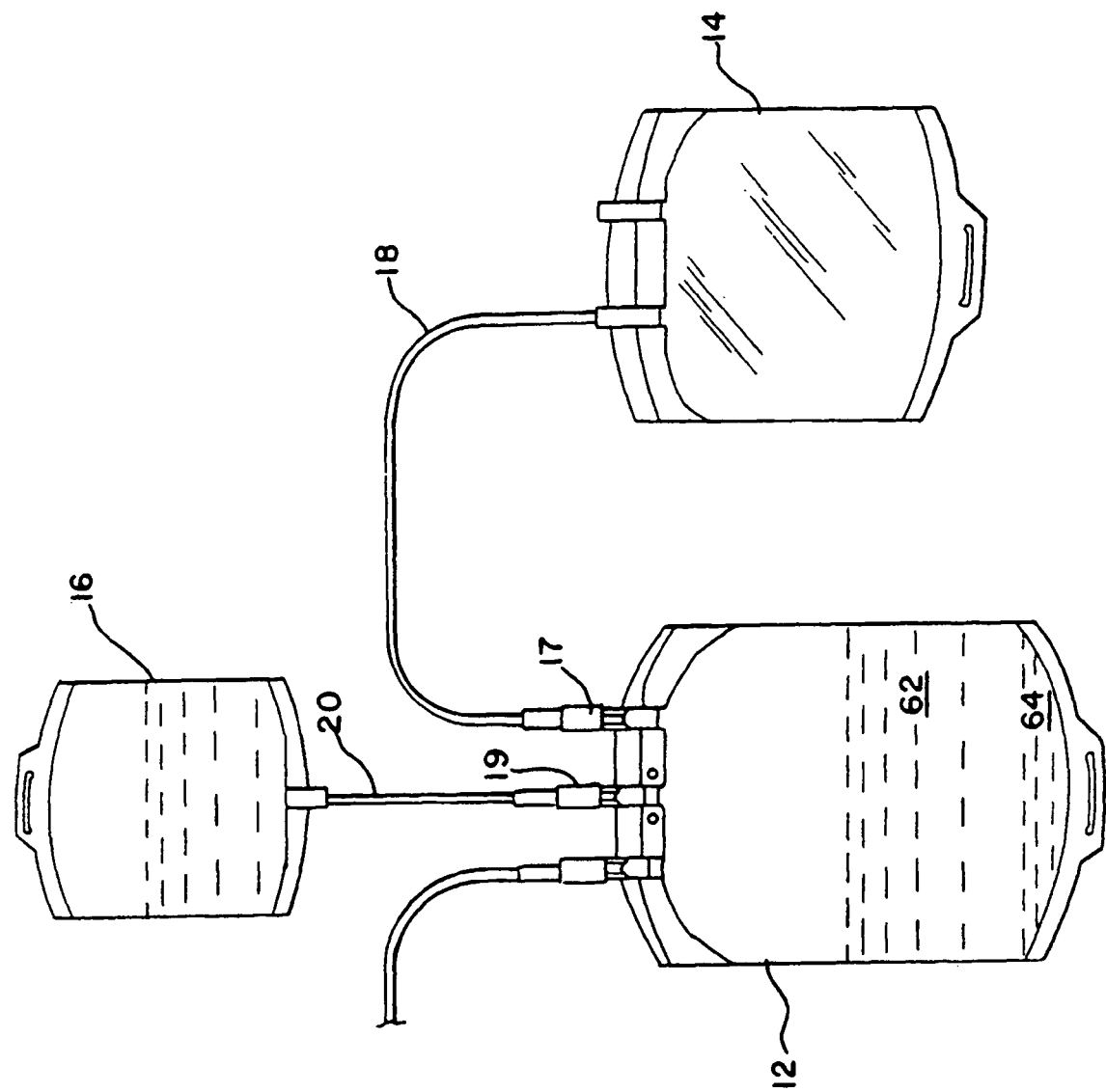
FIG. 6 is a plan view of the container system of FIG. 1 after separation of the source platelets into plasma and platelet concentrate in the interim container.
Figure 7:
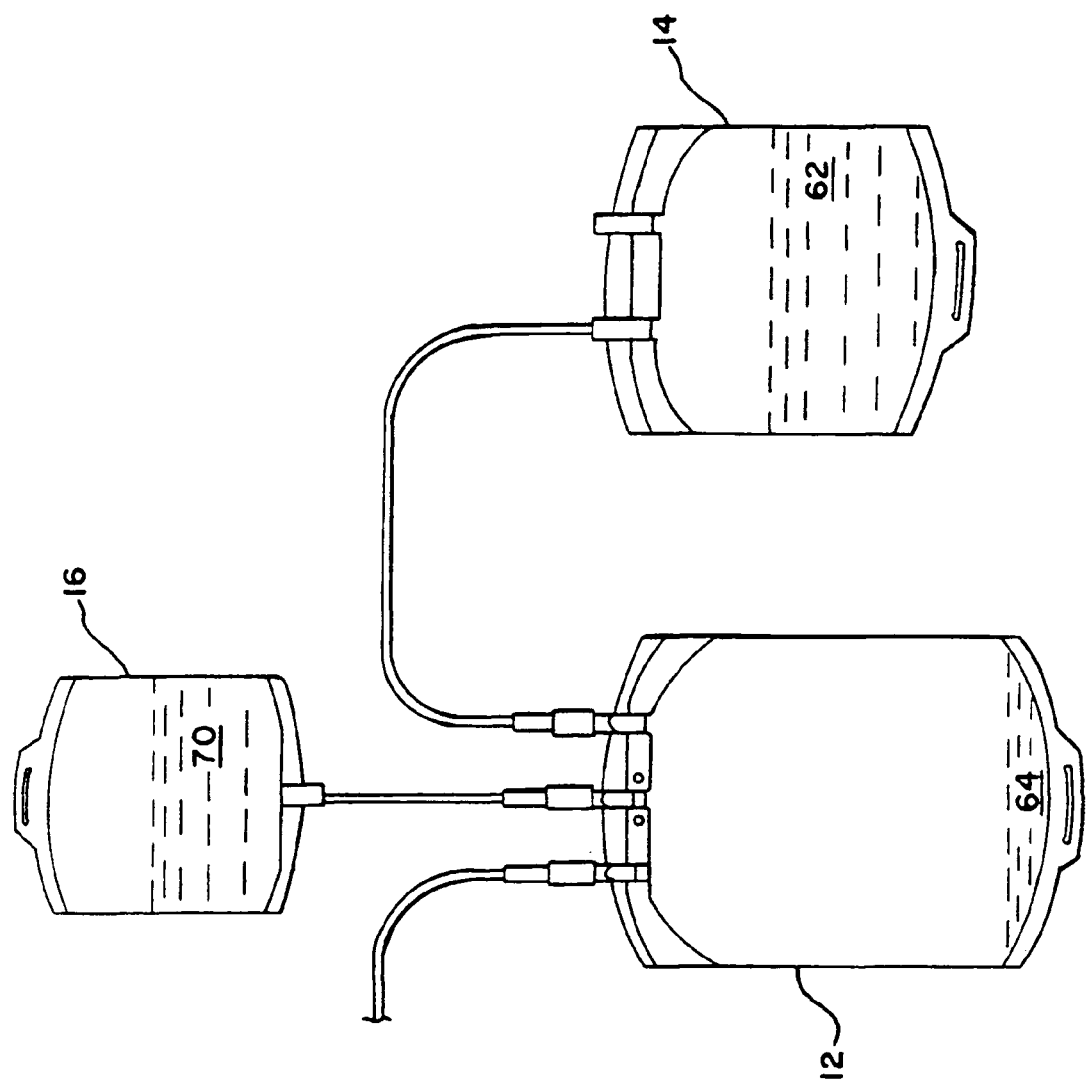
FIG. 7 is a plan view of the container system of FIG. 1 after removal of separated plasma from interim container and transfer to excess fluid container.

In any event, upon centrifugation, plasma generally forms in upper layer 62 in interim container 12 and platelet concentrate suspended in some plasma 64 forms the bottom layer, as shown in FIG. 6. Upper plasma layer 62 may then be expressed from interim container 12 through tubing 18 (by opening flow control device 25) to excess fluid container 14, as generally shown in FIG. 7. The excess plasma may be expressed manually, by simply squeezing the container to remove the plasma layer or, more preferably, using devices specifically designed for expression of separated layers of biological fluid. Such devices are known to those of skill in the art and are available from Baxter Healthcare Corporation of Deerfield, Ill.

The quantity of plasma 62 removed from interim container 12 or the amount of platelet concentrate in plasma remaining may be determined by weighing either interim container 12 or excess liquid container 14. For example, in one embodiment, where the original platelet source includes 300 ml of platelets in plasma, (after centrifugation) excess plasma is removed from interim container 12 until it is determined, by weighing, that the volume remaining in interim container is approximately 105 ml platelets in plasma, or that the volume of plasma removed from interim container is approximately 195 ml.

Figure 8:
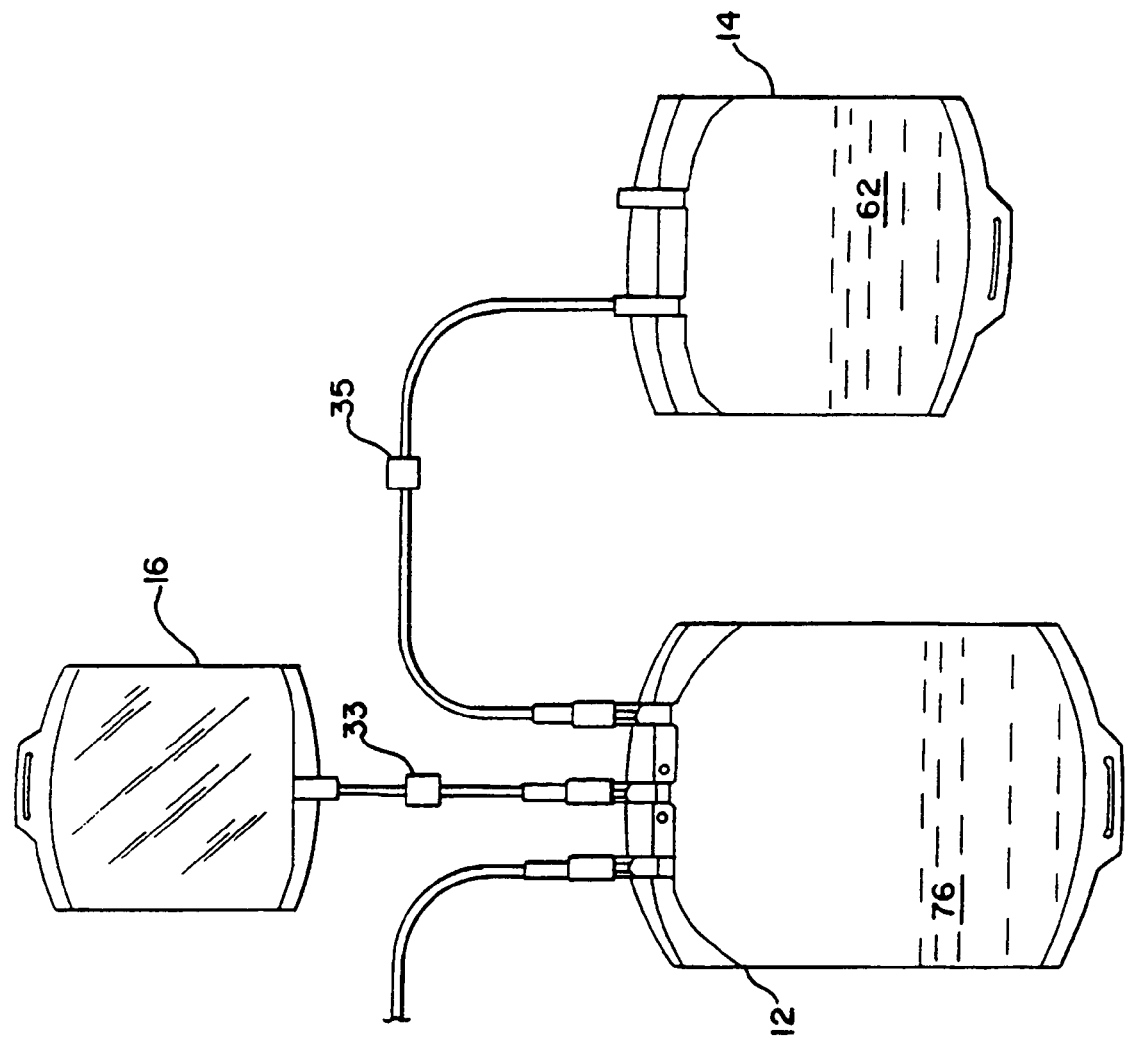
FIG. 8 is a plan view of the container system of FIG. 1 after addition of a synthetic storage medium to the interim container.
Figure 9:
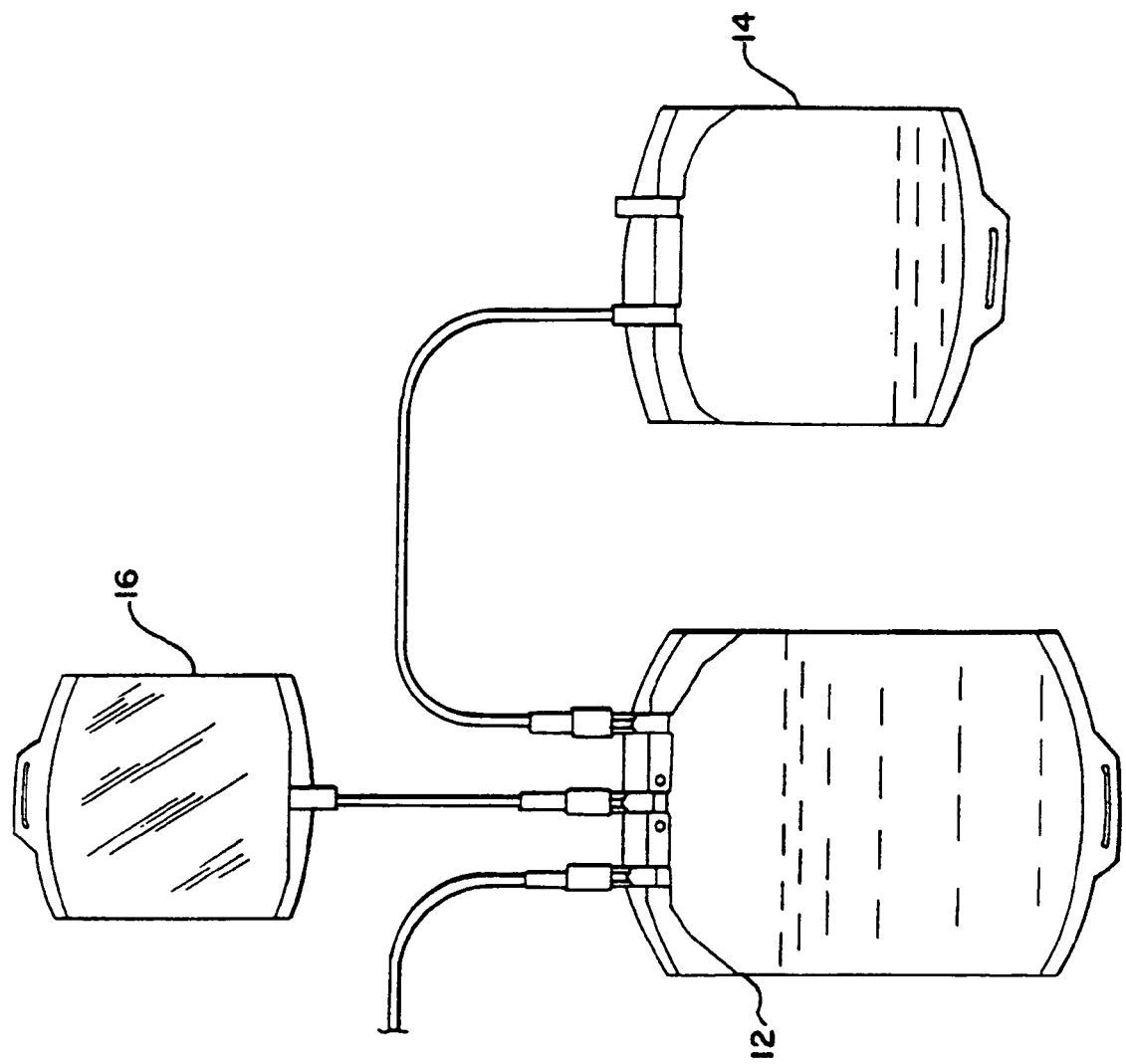
FIG. 9 is a plan view of the container system of FIG. 1 after addition of plasma from excess fluid container to the interim container.

Once excess plasma 62 has been removed from interim container 12, flow control device 23 is opened and synthetic storage medium 70 from container 16 may be introduced into interim container 12, as shown in FIG. 8. In the specific embodiment described above, where the volume of platelet concentrate in plasma is approximately 105 ml, the volume of synthetic storage medium added may be approximately 195 ml, thus providing a platelet concentrate in synthetic storage medium and plasma 76 (FIG. 8). Thus, the quantity of synthetic medium to be added may be determined by the quantity of plasma removed. The quantity of the synthetic medium to be added may also be determined by monitoring the weight of container 16 as medium is transferred, or by simply observing the changing fluid level in containers 12 and/or 16. In one embodiment, synthetic storage medium container 16 may be filled with 195 ml of the medium, thus ensuring that by completely emptying container 16, the required amount of media has been added to achieve the required ratio of medium and plasma. Flow control devices 23 and 25 may also optionally be used in association with tubing 18 and 20 to control the flow of plasma and/or storage medium from the containers.

Once the synthetic storage medium has been added to interim container 12, if necessary, some additional plasma 62 from excess fluid container 14 may be added back, as desired, to interim container 12 to achieve the selected ratio of synthetic storage medium to plasma. In any event, as indicated above, in one established protocol for the pathogen inactivation of platelets, the ratio should be between approximately 60–70% storage medium to 30–40% plasma. More preferably, the platelets are suspended in a ratio of 65:35 synthetic storage medium to plasma.

Once combined with platelet storage medium and plasma in the desired quantities and ratio, the platelet product is now treatment-ready and may be connected (in, for example, a sterile manner) to a pathogen inactivation system as generally shown in FIG. 10. The platelet product may be transferred from the interim container 12 of set 28 to a disposable processing set designed for pathogen inactivation treatment. An example of such a processing set is described in U.S. Ser. No. 09/325,599, filed on Jun. 3, 1999 and which is incorporated herein by reference. The interim container 12 may be attached via one of the existing tubings 18, 20, 22 or a separate dedicated tube (not shown) to set 28 which includes a container 40 holding a photochemical compound and a treatment container 42. The disposable processing set may include additional containers required in the pathogen inactivation treatment.

Figure 3:
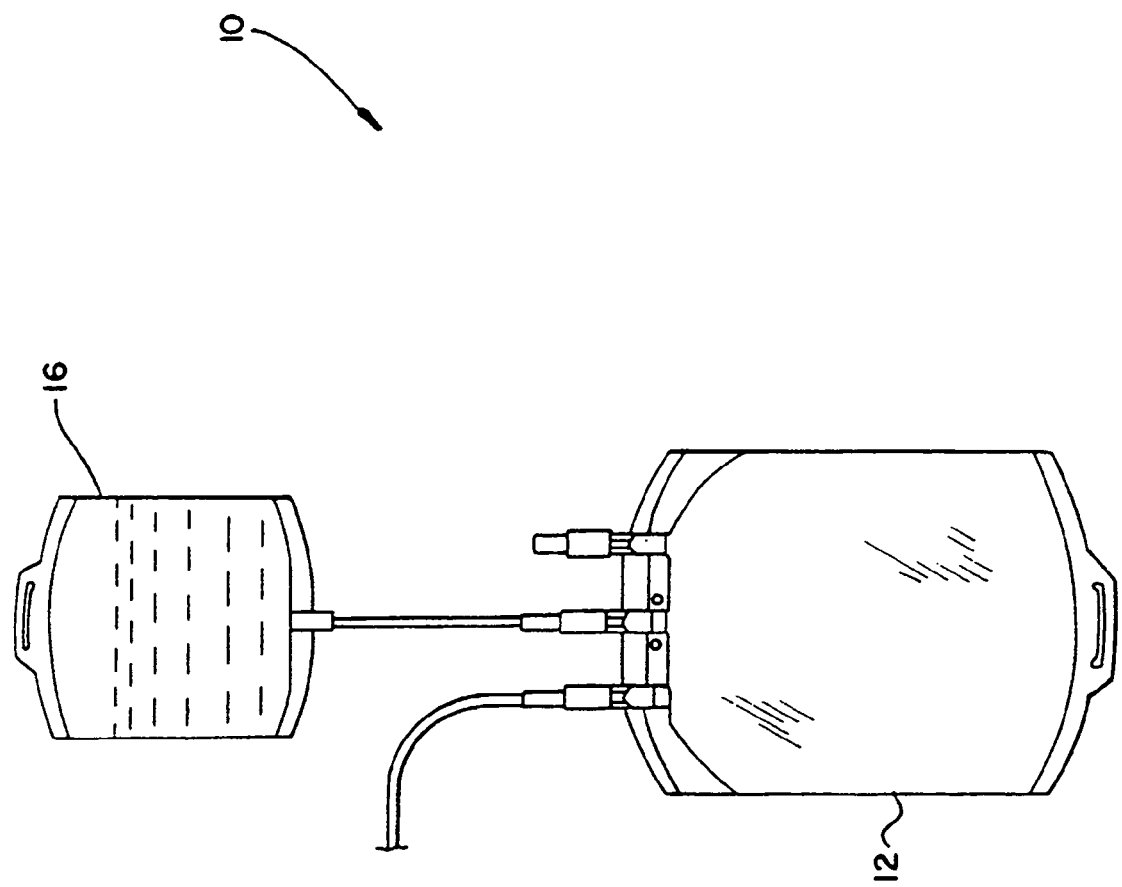
FIG. 3 is a plan view of another alternative container system embodying the present invention.
Figure 4:
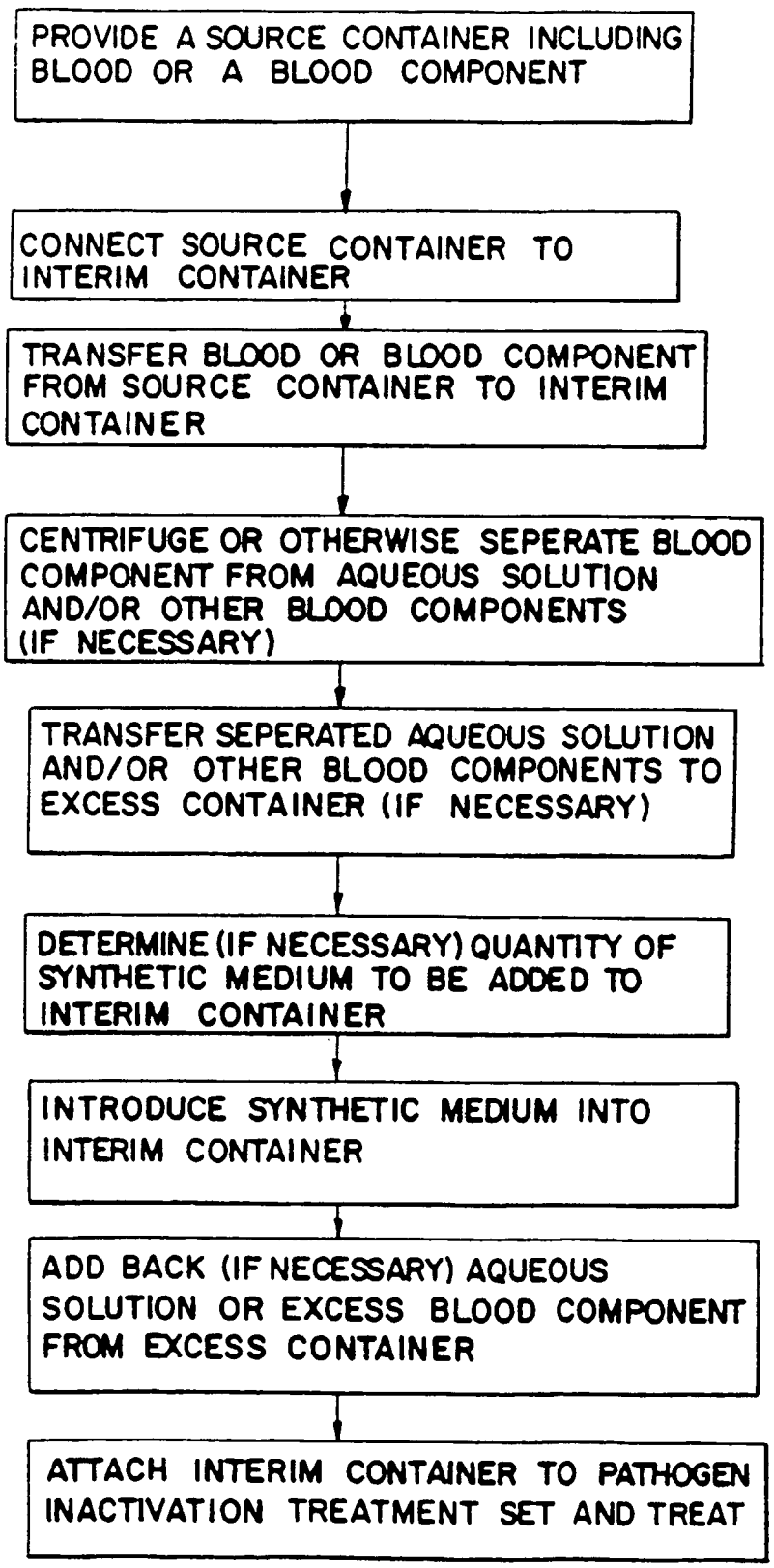
FIG. 4 is a flow diagram showing the steps embodying the method of the present invention.

It will be recognized that other embodiments are also possible without departing from the scope of the present invention. In an alternative embodiment, if the platelets in the source container 30 are substantially concentrated, the separation step may not be necessary. Thus, as shown in FIG. 3, container system 10 may not include an excess fluid container 14 for receiving excess plasma. In this embodiment, the therapeutic dose of platelets with some but not much residual plasma may simply be transferred to interim container 12 with no further separation step required.

Thus, if the volume of plasma in the therapeutic dose of platelets collected by apheresis is discernable and no further separation step is required, a selected amount of synthetic storage medium may be added to obtain the desired ratio of 65:35 storage medium to plasma. The platelet product may then be ready for attachment to a pathogen inactivation treatment set for treatment therein.

Likewise, if a blood product other than platelets is being prepared, no further separation (by centrifugation or other means) may be required. For example, if a treatment-ready plasma product is being prepared, further separation may or may not be required, depending on the quantity of any residual blood components (red cells, platelets) present. Similarly, if a treatment-ready red blood cell product is being prepared, further separation may not be required. Thus, in either case, there may or may not be a need for an excess fluid container.

In another embodiment, where the source of platelets is sufficiently concentrated and the volume of plasma with the source platelets is known, interim container 12 may already include the required volume or quantity of the synthetic storage medium. Thus, concentrated platelets may be transferred from a source container to the interim container which already includes the synthetic storage medium in the required or desired quantity. Thus, in this embodiment, no further processing is required prior to connection of the interim container including the platelet product to the disposable processing set for pathogen inactivation.

The foregoing description has been offered for illustrative purposes only, and it will be appreciated that further modifications of the embodiments and methods are possible without departing from the invention which is set forth in the appended claims.

That which is claimed:

1. A method for preparing a pathogen inactivation treatment-ready blood product comprising:
   providing a container system comprising at least a pre-connected interim container, a container including a liquid synthetic medium, and a transfer container wherein said medium container and said transfer container are in openable flow communication with said interim container;
   providing a source container including a quantity of a blood component derived from an apheresis procedure, said source container being separate from the container system;
   establishing fluid communication between said source container and said interim container,
   transferring said apheresis-derived blood component to said interim container;
   centrifuging said interim container to substantially separate said blood component into said blood component and a supernatant component;
   substantially removing said supernatant component from said interim container and transferring the same to said empty transfer container;
   determining the amount of the supernatant component remaining with said blood component; and
   combining a selected quantity of said blood component with a selected quantity of said synthetic medium within said interim container to provide a blood product with a pre-selected ratio of said supernatant component to said synthetic medium effective for said pathogen inactivation treatment.

2. The method of claim 1 wherein said blood component substantially comprises red blood cells.

3. The method of claim 1 wherein said blood component substantially comprises platelets and plasma.

4. The method of claim 1 comprising determining the quantity of said synthetic medium required for combination with said blood component to achieve said selected ratio of blood component to synthetic medium prior to said transferring.

5. The method of claim 1 in which said step of establishing fluid communication between said source and interim containers is carried out in an essentially sterile manner.

6. The method of claim 5 in which a sterile connection device is employed.

7. The method of claim 1 further comprising adjusting the amount of said supernatant in said interim container after said determining step.

8. The method of claim 7 further comprising transferring an amount of said supernatant from said transfer container back to said interim container after said determining.

* * * * *

UNITED STATES PATENT AND TRADEMARK OFFICE
CERTIFICATE OF CORRECTION

| | | |
|---|---|---|
| PATENT NO. | : 6,936,413 B1 | Page 1 of 1 |
| APPLICATION NO. | : 10/004696 | |
| DATED | : August 30, 2005 | |
| INVENTOR(S) | : Daniel F. Bischof and Ying-Cheng Lo | |

It is certified that error appears in the above-identified patent and that said Letters Patent is hereby corrected as shown below:

Col. 9, line 53, delete ""9" forces" insert --"g" forces--.

Signed and Sealed this

Third Day of April, 2007

JON W. DUDAS
*Director of the United States Patent and Trademark Office*